(12) United States Patent
Hielm

(10) Patent No.: US 7,938,464 B1
(45) Date of Patent: May 10, 2011

(54) DOOR OPENING DEVICE FOR A HANDICAPPED PERSON

(76) Inventor: Earl A. Hielm, Port Charlotte, FL (US)

( * ) Notice: Subject to any disclaimer, the term of this patent is extended or adjusted under 35 U.S.C. 154(b) by 377 days.

(21) Appl. No.: 12/274,723

(22) Filed: Nov. 20, 2008

(51) Int. Cl.
*B25J 1/04* (2006.01)

(52) U.S. Cl. .............................. 294/1.1; 294/26; 16/413

(58) Field of Classification Search ................... 294/1.1, 294/19.1, 22, 24, 26; 16/413, 426, 427
See application file for complete search history.

(56) References Cited

U.S. PATENT DOCUMENTS

| | | | |
|---|---|---|---|
| 2,027,009 A | | 1/1936 | Wyscaver |
| 2,732,739 A | | 1/1956 | Liss |
| 3,819,221 A | * | 6/1974 | O'Connor ........................ 81/484 |
| 4,686,742 A | * | 8/1987 | Arnold ............................ 16/438 |
| D325,688 S | | 4/1992 | Schreib |
| 5,231,733 A | * | 8/1993 | Dittman ......................... 16/412 |
| 5,314,221 A | * | 5/1994 | Hammer ...................... 294/19.1 |
| 5,540,468 A | | 7/1996 | Fassman |
| 5,555,779 A | | 9/1996 | Holden |
| 6,293,601 B1 | * | 9/2001 | Johnson .......................... 294/26 |
| 6,499,778 B2 | * | 12/2002 | Boulay ............................ 294/26 |
| 7,178,845 B1 | | 2/2007 | Metzger et al. |
| 7,309,088 B2 | * | 12/2007 | Fiore et al. ....................... 294/24 |
| D560,473 S | | 1/2008 | Wolfe, Jr. |
| D624,801 S | * | 10/2010 | Radloff .......................... D8/308 |
| 2004/0100109 A1 | * | 5/2004 | Johnson .......................... 294/26 |

* cited by examiner

*Primary Examiner* — Dean J Kramer
(74) *Attorney, Agent, or Firm* — Charles J. Prescott

(57) ABSTRACT

A manually manipulated assistive device for facilitating opening and closing a door by a handicapped person, especially one in a wheelchair. An elongated slender body preferably formed of a single transparent rigid plastic rod has a straight central portion, a hook formed at one end like a shepherd's hook and a hand or finger grasping handle at another end of the rod. The hook is adapted for snug snapping engagement over a neck area of a doorknob and, thereafter, for loose swinging supported movement relative to the doorknob. The rod has a length sufficient for the device to be held and pivoted on the hook about the neck area into a generally horizontal position by user grasping the handle to open or close the door. A retaining clip attached to the door at a height above the floor similar to that of the doorknob holds the device in a generally horizontal orientation stored ready for use.

4 Claims, 5 Drawing Sheets

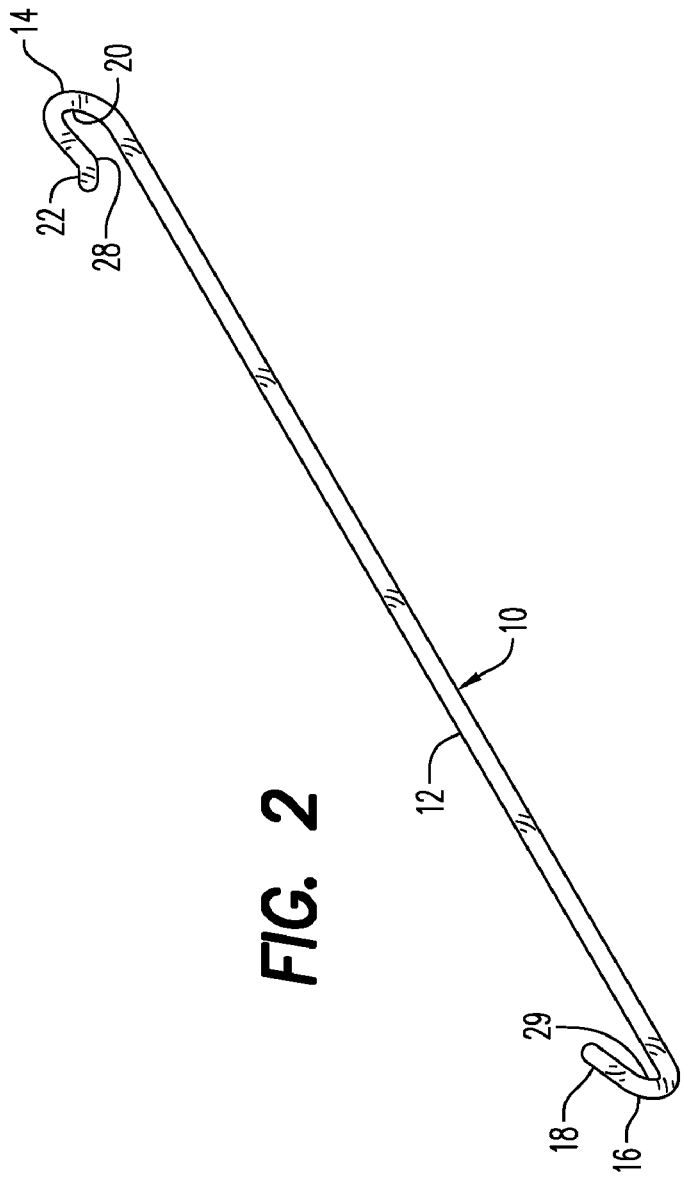
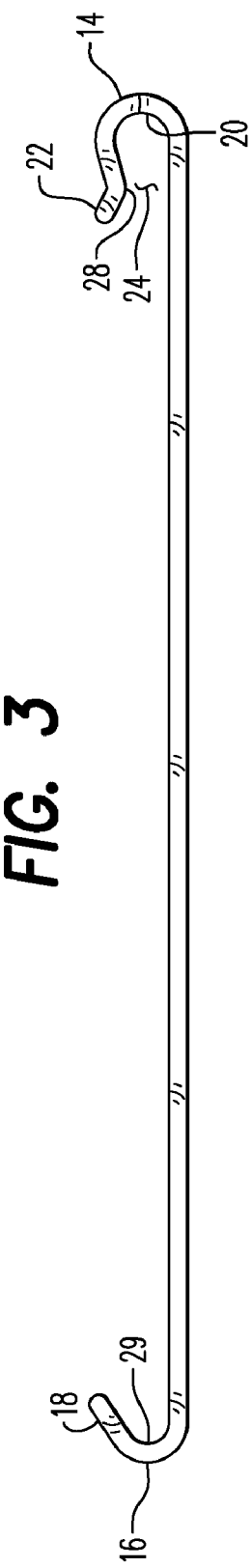
FIG. 2
FIG. 3

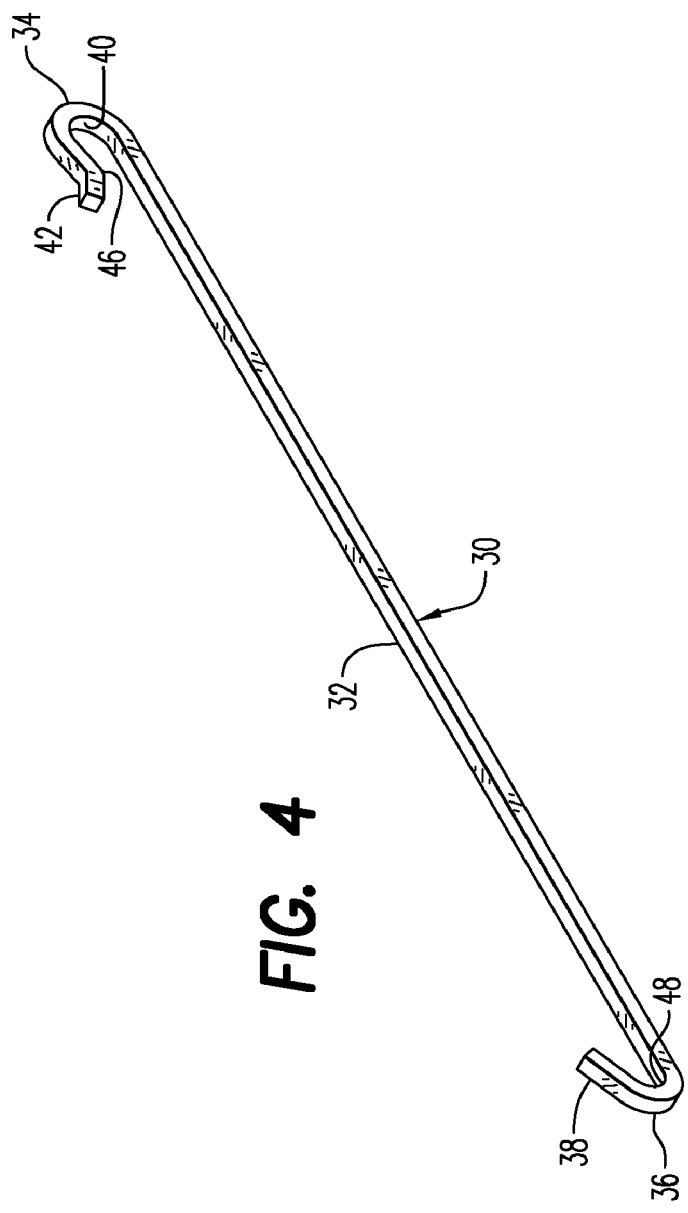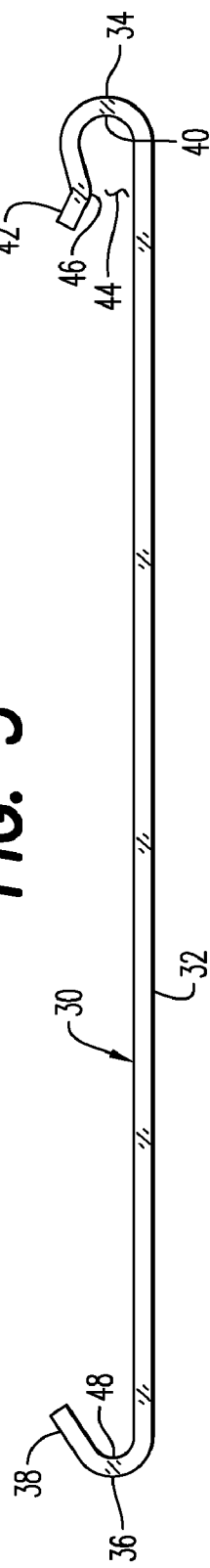

DOOR OPENING DEVICE FOR A HANDICAPPED PERSON

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to adaptive devices for assisting the handicapped in performing routine daily activities, and more particularly to a device which facilitates the opening and closing of a door by a physically impaired user confined to a wheelchair or a walking aid such as crutches or a walker for mobility.

2. Description of Related Art

The ease and convenience in performing routine activities in daily living by a physically impaired or handicapped person is continually evolving and improving. Even the smallest of activities that the able-bodied take for granted can be extremely difficult for someone who is handicapped and either wheelchair bound or requiring walking aids such as crutches or a walker. A routine task of simply opening or closing a door is readily taken for granted by the able bodied but can represent a significant challenge to a handicapped person required, for example, to use a wheelchair for mobility.

An invention by Fassman disclosed a U.S. Pat. No. 5,540,468 teaches a door opening and closing device for handicapped persons which is aimed at simplifying this challenging task for a wheelchair-limited person. A flexible cord retracting wheel is held by the hand or around the wrist of a user, while a hook at the end of a flexible member extendable from the wheel is engageable around the shaft of a doorknob so that the user may then easily close the door without being in the way of the closing door.

U.S. Pat. No. 7,178,745 to Metzger, et al. teaches a similar device. This hand-held article is useful for grasping door handles with a hook-like extremity and the unit is stowable when not in use.

U.S. Pat. No. 2,732,739 to Liss teaches an automobile entry tool and Holden teaches a door opener for individuals in a wheelchair in U.S. Pat. No. 5,555,779. U.S. Pat. No. 2,027,009 to Wyscaver teaches a tool for opening automobile doors and U.S. Design Pat. D560,473 to Wolfe, Jr. discloses a double-ended hook. Design Pat. Des. 325,688 to Schreib teaches a combined hook and pusher pole.

The present invention discloses a rigid elongated door opening and closing assistive device formed preferably of a single slender elongated rod having a hook and a handle formed at opposite ends, respectively, of the rod. The hook is in the form of a shepherd's hook which will resiliently snap around and be retained on the neck area of the doorknob. The handle is hand or finger graspable by the user and preferably includes a radiused V-shape configuration adapted in size to easily receive a finger of the user for facilitating grasping and pulling to effect door closure. A separate retaining clip is attachable to the door at about the height of the doorknob so that the device may be stored when not in use in a generally horizontal position with the handle being positioned in proximity to the hinged edge of the door in a position for ready use by the wheelchair user.

The foregoing examples of the related art and limitations related therewith are intended to be illustrative and not exclusive. Other limitations of the related art will become apparent to those skilled in the art upon a reading of the specification and a study of the drawings.

BRIEF SUMMARY OF THE INVENTION

This invention is directed to a manually manipulated assistive device for facilitating opening and closing a door by a handicapped person in a wheelchair. An elongated slender body preferably formed of a single transparent rigid rod has a straight central portion, a hook formed at one end like a shepherd's hook and a hand or finger grasping handle at another end of the rod. The hook is adapted for snug snapping engagement over a neck area of a door handle and, thereafter, for loose swinging supported movement relative to the doorknob. The rod has a length sufficient for said device to be held and pivoted on the hook about the neck area into a generally horizontal position by user grasping the handle to open or close the door. A retaining clip attached to the door at a height above the floor similar to that of the doorknob holds the device in a generally horizontal orientation stored ready for use.

It is therefore an object of this invention to provide a door opening and closing assistive device which will loosely but retentively engage around the neck area of a doorknob of a door to be opened and closed by the device which assists a handicapped person in a wheelchair, on crutches, or in a walker.

Still another object of this invention is to provide an assistive device which is easily installable around the neck of a doorknob and will be retained in place in a generally horizontal orientation with the handle of the device in proximity to the hinged edge of the door for easy access by the handicapped user.

Yet another object of this invention is to provide a door opening and closing assistive device for use by the handicapped which does not require any tools or door or doorknob modification for installation and use.

The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements. In addition to the exemplary aspects and embodiments described above, further aspects and embodiments will become apparent by reference to the drawings and by study of the following descriptions.

BRIEF DESCRIPTION OF THE SEVERAL VIEWS OF THE DRAWING(S)

FIG. 2 is a perspective view of the device shown in FIG. 1.

FIG. 3 is a side elevation view of FIG. 2.

FIG. 4 is a perspective view of another embodiment of the invention.

FIG. 5 is a side elevation view of FIG. 4.

Exemplary embodiments are illustrated in reference figures of the drawings. It is intended that the embodiments and figures disclosed herein are to be considered to be illustrative rather than limiting.

DETAILED DESCRIPTION OF THE INVENTION

Figure 1:
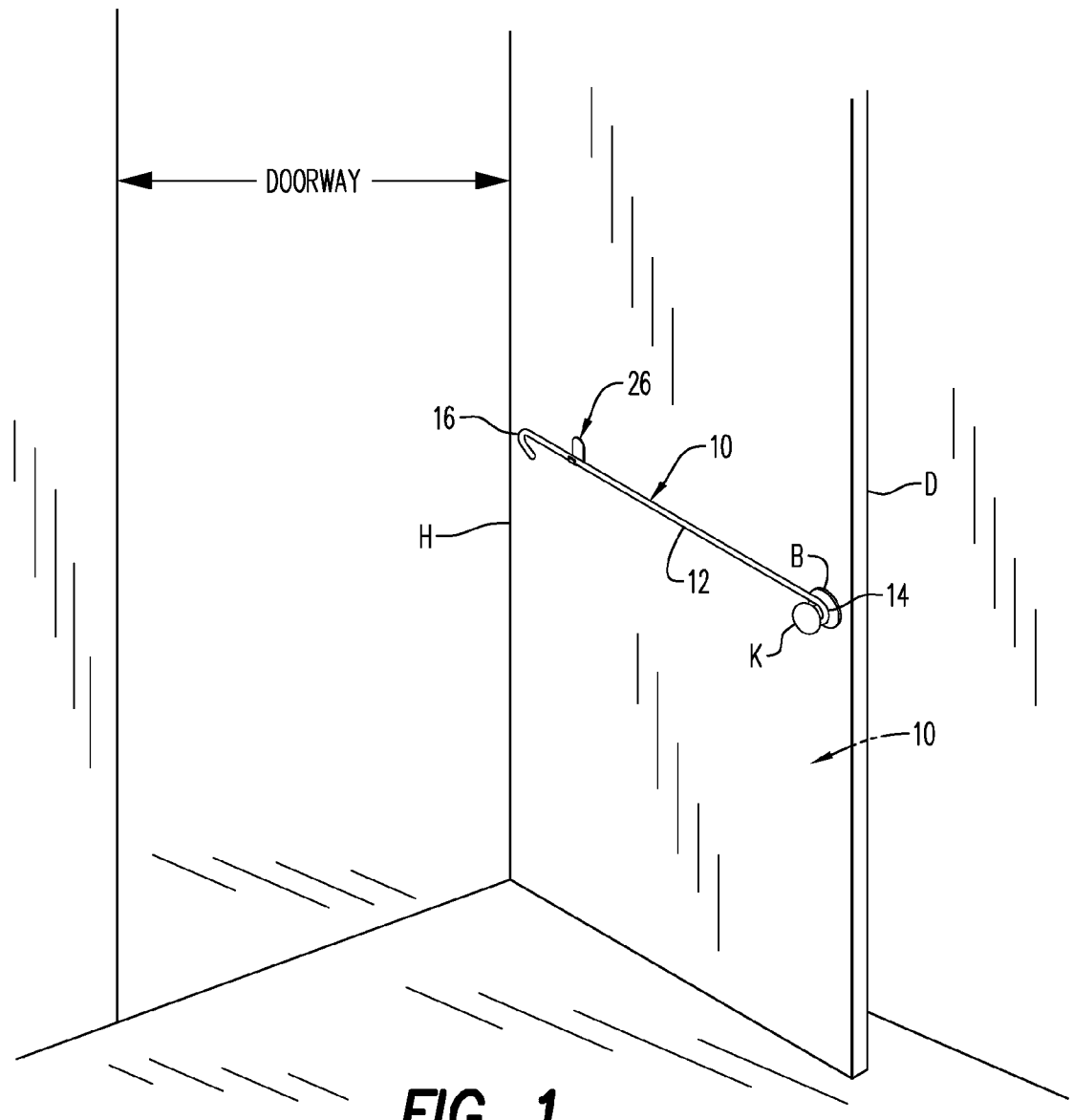
FIG. 1 is a perspective view of a typical door and doorway showing the invention installed on the door ready for use.

Referring now to the drawings, and firstly to FIGS. 1 to 3, a typical doorway and hinged door D are shown in FIG. 1, the door D being shown in the open position. One embodiment of the invention is shown generally at numeral 10 attached to the door D between a doorknob K and a retaining clip 26 which has been adhesively attached to the inward facing surface of the door D at a height above the floor approximately equal to that of the doorknob K.

The assistive device 10 is formed of an elongated length of preferably cylindrical transparent polycarbonate plastic rod 12, the transparency reducing the overall appearance of the device 10 when in place ready for use on the door as shown in FIG. 1. One end of the elongated rod 12 is formed into a hook 14 having a shape generally similar to that of a shepherd's hook. The elongated rigid or semi-rigid rod has a straight central portion, the hook 14 formed at one end and a hand or finger grasping handle 16 formed at another end of the rod 12. The hook 14 is adapted for snug snapping engagement over a neck A of a doorknob K and, thereafter, for loose swinging supported movement relative to the doorknob K.

Figure 6:
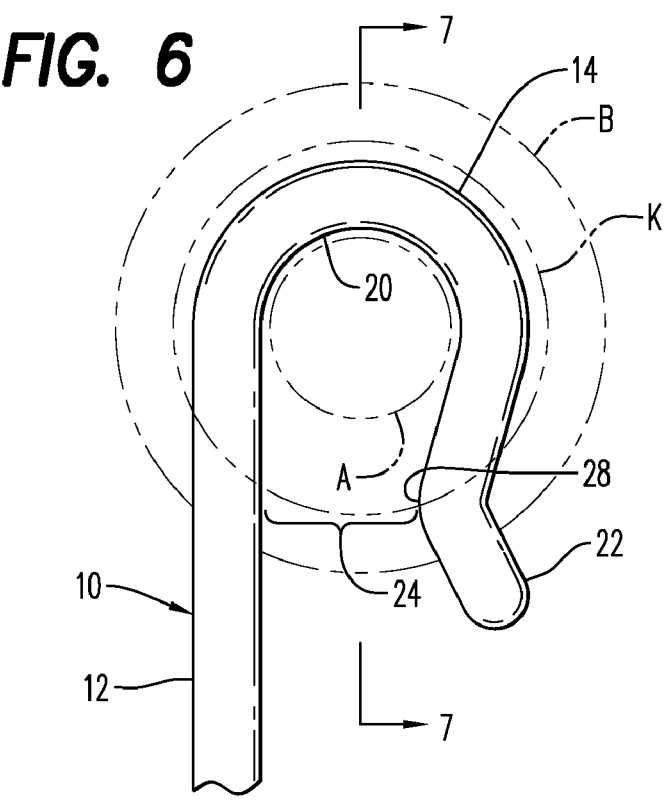
FIG. 6 is an enlarged elevation view of a typical doorknob shown in phantom with the hook end of the device retained in the in-use position around the neck of the doorknob.
Figure 7:
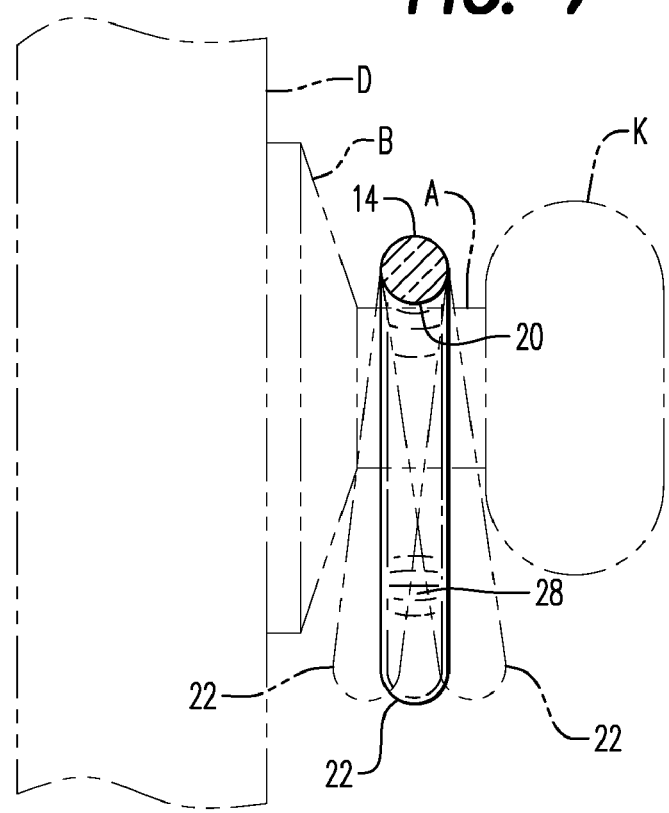
FIG. 7 is a section view in the direction of arrows 7-7 in FIG. 6.

The rod 12 has a length sufficient for said device 10 to be held and pivoted on the hook 14 about the neck A into a generally horizontal position by user grasping the handle 16 to open or close the door D. A retaining clip 26 is attached to the door at a height above the floor similar to that of the doorknob K and holds the device 10 in a generally horizontal orientation stored ready for use as shown in FIG. 1. The hook 14 has an inside radius 20 which, as seen in FIGS. 6 and 7, generally equal to or slightly larger than the neck A of the doorknob K. This inner radius bend 20 extends through more than 180° terminating at bend 28, the distal tip 22 outwardly extending to facilitate easy resilient engagement of the hook 14 around the neck A of the doorknob K. Thus, by forming the inner radius 20 to terminate at bend 28, a gap 24 is established which is narrower than the diameter of the neck A so that, when the rod 12 is pulled to attach the device 10 to the doorknob K, the gap 24 will resiliently expand to quickly effect installation of the hook 14 around the neck A into the position shown in FIGS. 6 and 7 without the need for tools. Once so installed, the device 10 is freely pivotable about the neck A in a rotational direction and in a lateral side to side direction shown in FIG. 7 to facilitate convenient use of the device 10 without being concerned about binding or breakage of either the device or the surface of the door bezel or doorknob. Moreover, the resiliency provided by the hook 14 renders it adaptable to a wide range of sizes of doorknob necks A.

The handle 16 which is preferably formed into a V-shaped configuration having an inner radius 29 which is selected to comfortably receive the finger of a user. Alternately, the user may grasp the straight distal portion 18 to effect use of the device 10 described herebelow.

Figure 1A:
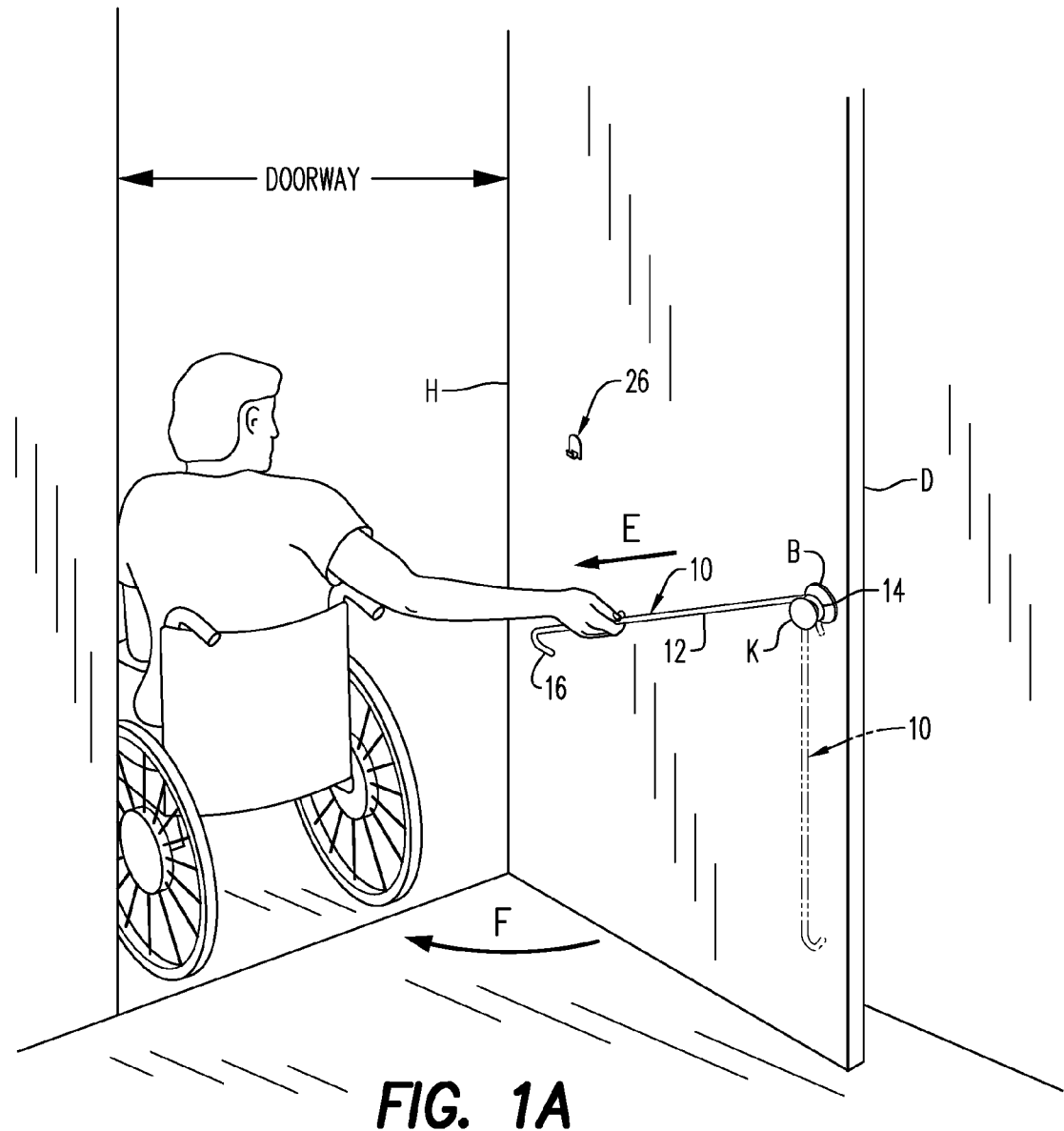
FIG. 1A is a view similar to FIG. 1 showing a wheelchair confined handicapped person using the device to close the door.

Referring particularly to FIG. 1A, the device 10 may easily be grasped by the user as shown from a stored position shown either downwardly hanging (in phantom) from the doorknob K or suspended in a generally horizontal position on clip 26 as shown and described previously in FIG. 1. Once the user has grasped the device as shown in FIG. 1A, a pulling motion in the direction of arrow E will effect closure of the door D in the direction of arrow F. Thereafter, the user may simply drop the device 10 back into the downwardly hanging position shown in phantom or the device may be reattached to clip 26 into the orientation shown in FIG. 1. Note that the device 10 may also be pushed in the opposite direction to re-open the door D as facilitated by the rigid or semi-rigid nature of the plastic rod 12 and the resilient retention of hook 14 around the neck A.

Referring lastly to FIGS. 4 and 5, an alternate embodiment of the device is there shown generally at numeral 30 formed of an elongated slender rigid or semi-rigid rod 32 having a generally square or rectangular cross-section. Again, the rod 32 is preferably formed of transparent or translucent material for reduced visibility or obtrusiveness of the device against the door D. The formed shepherd's hook 34 is disposed at one end of the plastic rod 32 to define a radius 40 sized as previously described to fit around the neck A of a doorknob K. Bend 46 effects resilient retention of the hook 34 around the neck A of the doorknob while outturned distal portion 42 facilitates easy resilient installation of the hook 34 around the doorknob neck A as previously described.

Disposed at the opposite end of rod 32 is a formed handle 36 which is bent arcuately to define an inner radius 48 which comfortably receives the sectional size of a finger of a user. Alternately, the straight distal portion 38 may be grasped by two or more of the fingers of a hand of the user to facilitate manipulation of the device to open or close the door D or to reinstall it into the retaining clip 26 shown in FIG. 1.

It will be appreciated that a preferred overall shape of this invention is flat or planar. With a formed hook disposed at one end and a formed handle at the other end of the slender rod, to achieve a device of this structure which compactly lays against the door without sticking out too far, it is preferred that all of these structural features lay in a single plane. While a number of exemplary aspects and embodiments have been discussed above, those of skill in the art will recognize certain modifications, permeations and additions and subcombinations thereof. It is therefore intended that the following appended claims and claims hereinafter introduced are interpreted to include all such modifications, permeations, additions and subcombinations that are within their true spirit and scope.

The invention claimed is:

1. A door opening and closing assistive device comprising:
an elongated slender substantially rigid body formed of a single rod and having a substantially straight central portion, a hook formed at one end thereof, and a hand or finger grasping handle at another end of said rod;
said hook being adapted for snapping engagement over a neck area of a doorknob and, thereafter, for loose swinging supported movement relative to the doorknob;
said rod having a length sufficient for said device to be pivoted on said hook about the neck area into a generally horizontal position by a physically impaired user grasping said handle to close the door;
a retaining clip attached or attachable to the door at a height above the floor similar to that of the doorknob for holding said device in a generally horizontal orientation with said handle positioned in close proximity to a hinged edge of the door ready for use.

2. A manually manipulatable assistive device facilitating opening and closing a door by a handicapped person in a wheelchair comprising:

an elongated slender body formed of a single transparent or translucent plastic rod and having a shepherd's hook-shaped hook formed at one end thereof, and a hand or finger grasping handle at another end of said rod;

said hook being shaped for resilient snapping retaining engagement over a neck area of a doorknob of the door and, thereafter, for loose swinging movement while being supported on the doorknob;

said handle being generally V-shaped with a radiused apex sized to receive a user's finger;

said rod having a length sufficient for said device to pivotally swing on said hook about the neck area into a generally horizontal position by the user grasping said handle to open or close the door;

a retaining clip attached to the door at a height above the floor similar to that of the doorknob for holding said device in a generally horizontal orientation with said handle positioned in close proximity to a hinged edge of the door ready for use.

3. The device of claim 2, wherein:
said body lies in a single plane.

4. The device of claim 3, wherein:
said body is transparent.

* * * * *